Feb. 2, 1960 C. A. ROWLAND, JR Plant Pat. 1,902
ILEX CRENATA PLANTS (JAPANESE HOLLY)
Filed May 8, 1959
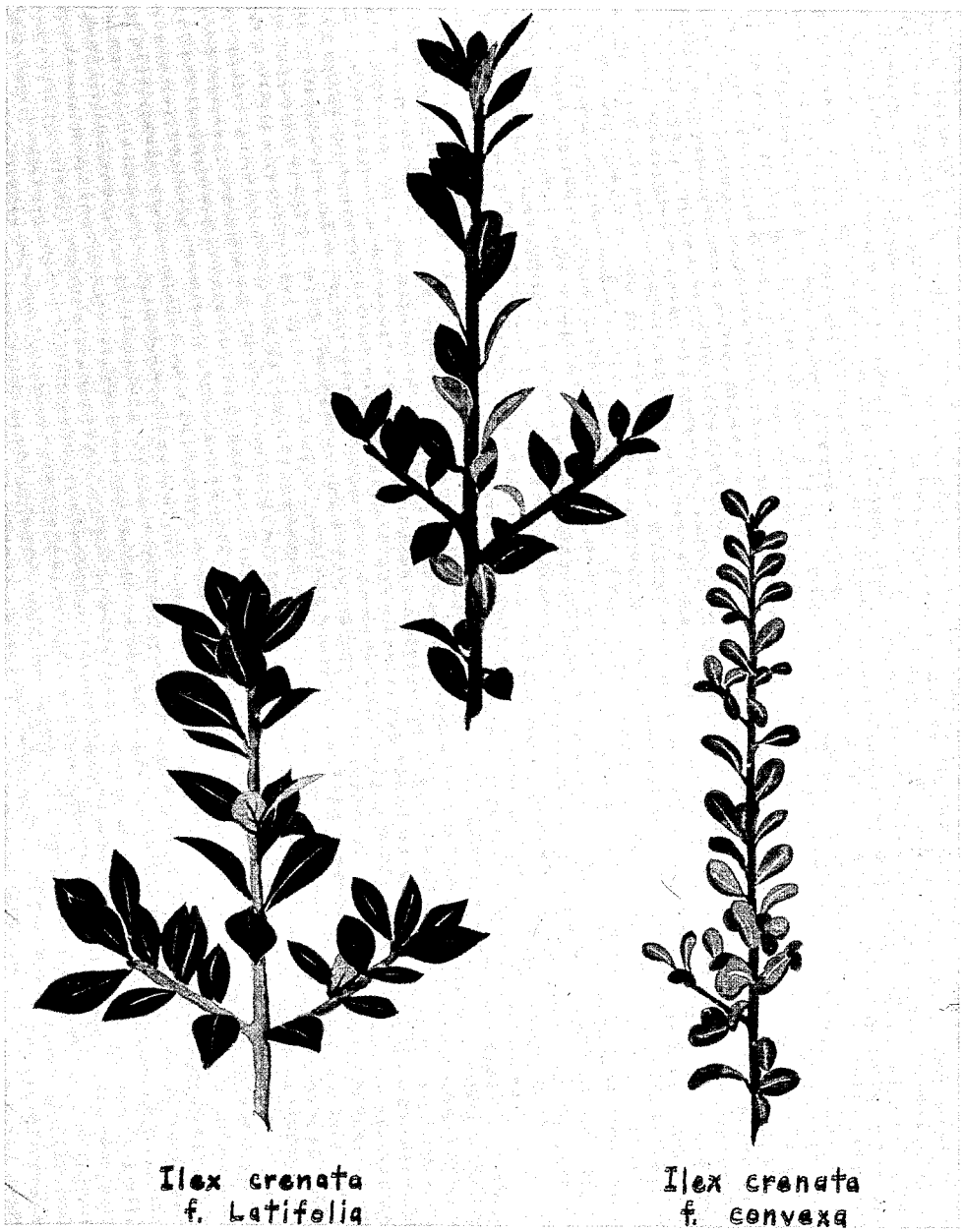
INVENTOR
Charles A. Rowland Jr.
By Orville M. Kile
Plant Patent Agt.

United States Patent Office

Plant Pat. 1,902
Patented Feb. 2, 1960

1,902

ILEX CRENATA PLANTS (JAPANESE HOLLY)

Charles A. Rowland, Jr., Athens, Ga.

Application May 8, 1959, Serial No. 812,076

1 Claim. (Cl. 47—59)

My present discovery relates to improvements in *Ilex crenata* varieties and originated as a seedling in my nurseries in Clarke County, Georgia, near Athens, where I grow and test many varieties of *Ilex crenata*. Although its parentage is not definitely known, its male parent was probably *Ilex crenata* f. Latifolia; and its female parent was doubtless *Ilex crenata* f. Convexa, as this was the only pistillate form in the nursery at the time. Asexual reproduction of my new variety has been accomplished at my nurseries in Clarke County, Georgia, by means of cuttings, and its outstanding characteristics appear to be permanent.

My new variety has some of the characteristics of each of its probable parents but its most outstanding features are the very dark, blue-green color and symmetrically elliptical form of its leaves, the size of which is midway between that of the leaves of the two probable parents; the dark, purplish-brown color of its stems in cool weather; and its ease of rooting and growth.

It differs from the typical species of *Ilex crenata* in the blue-green rather than yellow-green color of its leaves, in the dark color of its stems in cool weather, in its more divaricate branching, and in its ease of propagation.

The accompanying illustrations show in the upper central position, a branch of my new variety of *Ilex crenata* in approximately its true colors in cool weather. The varieties *Ilex crenata* f. Latifolia (lower left), and *Ilex crenata* f. Convexa (lower right) are pictured for comparative purposes only and show the relative leaf sizes and shapes, and the forms and colors of branches of the plants grown under similar conditions.

In the following detailed description, references to color plates indicate Ridgway's Color Standards and Nomenclature. Other reference to color indicates the ordinary dictionary meaning of the term.

Plant type: Staminate.

Growth habit: Very vigorous, upright grower.

Size: Medium. At 5 years of age, plants have attained a height of 3 to 4 feet and a diameter of 2 to 3 feet.

Form: Stiff and upright, with divericate branching.

Rooting: This variety possesses unusual ability to root easily from cuttings. Propagation in coarse sand over several seasons shows rooting success to be 95 to 100 percent from both medium-softwood and hardwood cuttings. Under identical conditions, f. Latifolia rooted 85 to 90 percent, and f. Convexa 75 to 80 percent. Survival of plants in the field shows approximately the same percentages.

Hardness: Resists low temperatures. Tests have been made as low as 6 degrees Fahrenheit with no ill effects to the plants.

Resistance to chlorosis: This new variety is much less affected by chlorosis than either of the other above-named varieties. In the bed of about 3,000 of each of the three varieties in my nurseries, there was no apparent chlorosis on the new variety. There was slight chlorosis on 25 percent of the f. Latifolia, and 100 percent of the f. Convexa were chlorotic. Whatever affected the f. Convexa variety so seriously had no effect upon the new variety.

Stems: Stiff. Branches spreading. New growth finely puberulent, with internodes approximately 3 to 5 mm. in length.

*Lenticels.*—Not noticeable.

*Color.*—Light yellowish-green (approximately Yellowish Oil Green, Plate V), turning dark purplish-brown with the first cool weather.

Flowers: Staminate and with no apparent difference from the flowers of the species.

Berries: Lacking.

Leaves:

*Type.*—Evergreen.

*Form.*—Symmetrically elliptical, with rounded base and obtuse apex. Flat to very slightly convex. Impressed midrib. Margin crenulate with 9 to 11 small appressed teeth on each side.

*Appearance.*—Upper surface glabrous, dull to shining, with pale midrib. Lower surface punctate, glabrous with slightly raised midrib. Lateral veins not noticeable.

*Substance.*—Leathery.

*Size.*—Blade 10 to 18 mm. long and 6 to 10 mm. wide.

*Petiole.*—Short, about 2 to 3 mm. long. Puberulent.

*Stipules.*—Triangular. Small. Fall off early.

*Color.*—Upper surface is dark bluish-green, between Dusky Green (Plate XXXIII) and Empire Green (Plate XXXII). Lower surface is lighter green, approximately Civette Green (Plate XVIII).

*Comparison*

The two varieties known to me which are most like my new variety are its probable parents, *Ilex crenata* f. Convexa and *Ilex crenata* f. Latifolia (sometimes known as Rotundifolia, Fortuneii, or Major). The chief differences are as follows:

My new variety differs from *Ilex crenata* f. Convexa principally in that:

(1) The branches of my new variety are more spreading.

(2) Its leaves are not convex above, and have a pointed apex, whereas the leaves of f. Convexa are convex and the apex is very rounded.

(3) Its leaves have a darker, blue-green color, and are slightly larger.

(4) It grows more vigorously and attains a considerably greater height.

(5) It roots much more readily.

(6) It transplants with much greater percentage of survival.

(7) Its stems are darker in cool weather.

(8) It is not affected by chlorosis, whereas test showed f. Convexa 100 percent affected under the same conditions.

(9) It is a staminate plant, whereas f. Convexa is pistillate.

My new variety differs from *Ilex crenata* f. Latifolia principally in that:

(1) It grows more vigorously, becoming slightly taller.

(2) Its leaves are darker in color.

(3) Its leaves are smaller and narrower.

(4) It roots more readily.

(5) It transplants with a greater percentage of survival.

(6) It is not affected by chlorosis while tests showed f. Latifolia to have been 25 percent affected under the same conditions.

(7) Color of its stems turn dark in cool weather whereas those of f. Latifolia remain light green.

Having thus disclosed my discovery, I claim:

The new and improved variety of *Ilex crenata* (Japanese holly) plant, substantially as herein shown and described, characterized particularly by its vigorous, upright growth and divaricate branching; its ease of rooting from cuttings and high percentage of survival from transplants; the almost complete absence of chlorosis; the dark purplish-brown color of its twigs and stems in cool weather; and the dark blue-green color and flat, symmetrically elliptical form of its leaves of medium size.

No references cited.